United States Patent [19]

Hoegnelid et al.

[11] Patent Number: 5,571,143
[45] Date of Patent: Nov. 5, 1996

[54] HEART STIMULATOR

[75] Inventors: Kurt Hoegnelid, Voesterhuninge; Hans Strandberg, Sundbyberg, both of Sweden

[73] Assignee: Pacesetter AB, Solna, Sweden

[21] Appl. No.: 467,267

[22] Filed: Jun. 6, 1995

Related U.S. Application Data

[63] Continuation of Ser. No. 147,744, Nov. 4, 1993, abandoned.

[30] Foreign Application Priority Data

Nov. 4, 1992 [SE] Sweden ................................. 9203284

[51] Int. Cl.⁶ ........................................................ A61N 1/00
[52] U.S. Cl. ................................................................. 607/9
[58] Field of Search ................................ 607/9, 18, 122, 607/123

[56] References Cited

U.S. PATENT DOCUMENTS

| | | |
|---|---|---|
| 3,903,897 | 9/1975 | Woollons et al. . |
| 3,977,411 | 8/1976 | Hughes, Jr. et al. . |
| 4,023,565 | 5/1977 | Ohlsson . |
| 4,154,247 | 5/1979 | O'Neill . |
| 4,213,465 | 7/1980 | Renheim . |
| 4,235,246 | 11/1980 | Weiss . |
| 4,245,643 | 1/1981 | Benzing, III et al. . |
| 4,567,901 | 2/1986 | Harris . |
| 4,630,611 | 12/1986 | King . |
| 4,760,852 | 8/1988 | Lekholm . |
| 4,799,486 | 1/1989 | DuFault . |
| 4,858,610 | 8/1989 | Callaghan et al. . |
| 5,085,224 | 2/1992 | Galen et al. . |
| 5,172,694 | 12/1992 | Flammang et al. . |
| 5,190,052 | 3/1993 | Schroeppel . |
| 5,235,977 | 8/1993 | Hirschberg et al. . |

FOREIGN PATENT DOCUMENTS

OS 29 52 818   7/1981   Germany .

*Primary Examiner*—William E. Kamm
*Assistant Examiner*—Scott M. Getzow
*Attorney, Agent, or Firm*—Hill, Steadman & Simpson

[57] ABSTRACT

A heart stimulator having a pulse generator and an electrode system, which contain at least one bipolar electrode with one pole arranged in the atrium and another pole in the ventricle, or at least two unipolar electrodes respectively arranged in the atrium and ventricle, for detecting atrial and ventricular activity includes an atrial measurement unit which is connected for measuring a signal between the two poles of the bipolar electrode, or between the two unipolar electrodes, and a ventricular measurement unit arranged to measure the signals between the ventricular pole (or electrode) and the housing of the stimulator.

7 Claims, 7 Drawing Sheets

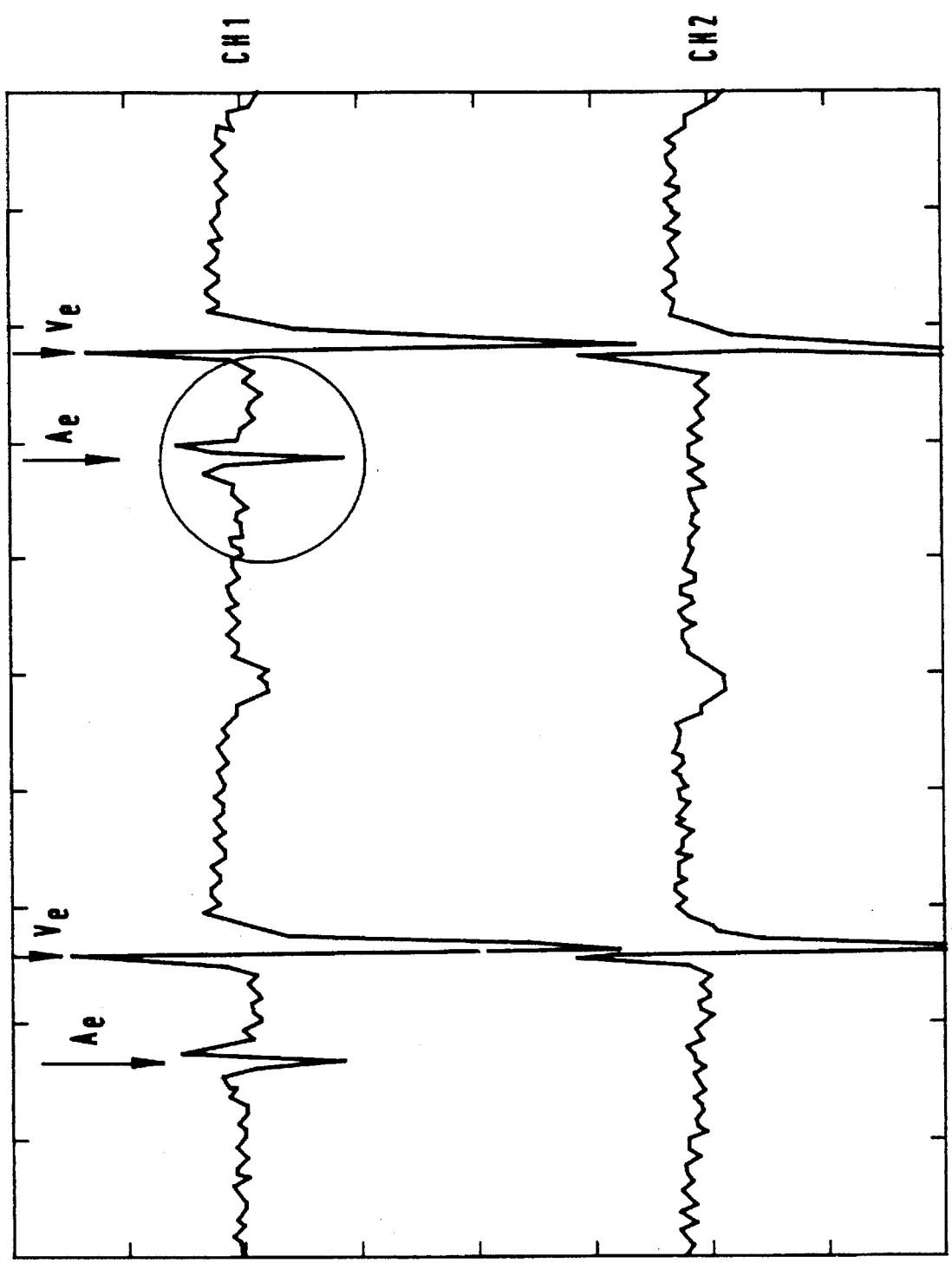

HEART STIMULATOR

This is a continuation of application Ser. No. 08/147,774, filed Nov. 4, 1993.

BACKGROUND OF THE INVENTION

1. Field of the Invention

The present invention is directed to a heart stimulator of the type having a pulse generator and an electrode system which contains at least one bipolar electrode with one pole arranged in the atrium and one pole in the ventricle, or at least two unipolar electrodes respectively arranged in the atrium and ventricle, for detecting atrial and ventricular activity.

2. Description of the Prior Art

Electrode systems of the type generally described above are disclosed in U.S. Pat. No. 4,154,247 and U.S. Pat. No. 4,567,901.

DDD pacemakers are currently used for treating patients with bradycardia. A conventional DDD pacemaker requires two electrodes, each with its own lead. One of the electrodes is placed in the atrium and the other in the ventricle. Electrical activity is sensed with the electrodes, and stimulation pulses are emitted when spontaneous electrical activity is not present.

There has long been a desire for DDD pacemakers employing only one electrode lead, i.e., a single lead DDD pacemaker. This would greatly simply implantation, compared to the currently required implantation of two separate and basically parallel leads.

The VDD pacemaker, using only one electrode with poles in the atrium and ventricle, is a step toward a single lead DDD pacemaker design. The poles in the atrium are "floating," i.e., they are normally not in direct contact with electrically active atrial tissue. The electrode system passes through both the atrium and the ventricle. This type of VDD electrode system contains three leads in instances wherein a unipolar electrode is employed in the ventricle, and contains four leads in instances wherein a bipolar electrode is employed in the ventricle.

SUMMARY OF THE INVENTION

It is an object of the present invention to provide a heart stimulator permitting detection of atrial and ventricular cardiac activity in a bipolar mode and having an electrode system employing a minimum number of poles or electrodes, plus attendant leads.

The above object is achieved in accordance with the principles of the present invention in a heart stimulator having a hear stimulating having a pulse generator and an electrode system which contains at least one bipolar electrode with one pole arranged in the atrium and one pole in the ventricle, or at least two unipolar electrodes respectively arranged in the atrium and ventricle, for detecting atrial and ventricular electrical activity, and having an atrial measurement unit arranged to measure a signal between the two poles of the bipolar electrode, or between the two unipolar electrodes, and a ventricular measurement unit arranged to measure a signal between the ventricular pole (or electrode) and the stimulator housing.

In the heart stimulator according to the invention, one lead terminates in a pole or electrode placed in the atrium, and a second lead terminates in a pole or electrode disposed in the ventricle. Atrial activity is sensed between the atrial pole or electrode and the ventricular electrode, while ventricular electrical activity is measured between the pole or electrode in the ventricle and the stimulator housing. In principle, a bipolar system for atrial detection is obtained when measurement of the atrial activity is between poles or electrodes in the atrium and in the ventricle. Atrial signals are often so weak that interference from muscular activity causes problems in measurements in the atrium, and bipolar electrodes have therefore often been used in the atrium in order to minimize such muscular interference. With the system according to the present invention, therefore, such a bipolar measurement system is achieved so as to avoid interference from muscular activity with no need for a bipolar electrode in the atrium.

Since ventricular events are also detected by the atrial measurement unit, whereas atrial electrical events are only detected by the atrial measurement unit, a logic unit is provided in a further embodiment of the heart stimulator of the invention, which approves the signal from the measurement unit as an atrial event only if the ventricular measurement unit fails to detect any signal occurring during a defined period of time around the time an atrial signal is measured. This particular technique is disclosed in Swedish Patent Application No. 9203171-5, corresponding to a U.S. Pat. No. 5,400,796.

In a further embodiment of the invention, a second pole arranged in the atrium is connected, through a resistor, to the lead for the ventricular pole. The resistor has a value in the range of 1–20 kohms. As a result of the resistor, this pole cannot be employed for stimulation in the atrium, because resistance is lower in the ventricular pole connected to the same lead. The value of the resistor must not be too low, however, otherwise the connected atrial pole would then draw current making stimulation through the ventricular pole more difficult or impossible. Even in this instance, ventricular activity is sensed via the ventricular pole, and atrial activity is sensed between the two atrial poles. This means that signals corresponding to both ventricular and atrial activity are carried by the same lead. The atrial signal, however, has a considerably lower amplitude than the ventricular signal because the voltage of the atrial signal is split (divided) because of the resistor. The sensitivity of the ventricular measurement unit is therefore set so that it detects the strong ventricular signals but not the weak atrial signals. Atrial activity is measured between the poles in the atrium, as noted above, and the logic unit approves the signal from the atrial measurement unit as a genuine atrial event only if no ventricular signal is contemporaneously present.

The division in the voltage of the detected atrial signal depends on the magnitude of the resistor used for the second atrial pole. If a 1 kohm resistor, for example, is used, about $\frac{1}{10}$ of the atrial signal reaches the heart stimulator. In practice, the ventricular electrode then also serves as the indifferent electrode for sensed atrial signals. The pole or poles in the atrium can be "floating," i.e., not be in direct contact with electrically active tissue, if they are only to be used for detecting electrical activity. If the electrode system is devised, however, so that the atrial pole, which is directly connected to its lead, is in direct contact with atrial tissue, the atrial pole can also be used for stimulating the atrium. This results in a single lead DDD pacemaker employing only two leads in the electrode cable.

If a bipolar electrode is employed in the ventricle, three leads are required within the electrode cable.

DESCRIPTION OF THE DRAWINGS

FIG. 8 shows the signals detected by the atrial and ventricular measurement units in the heart stimulator of the invention in experiments conducted with animals.

DESCRIPTION OF THE PREFERRED EMBODIMENTS

Figure 1:
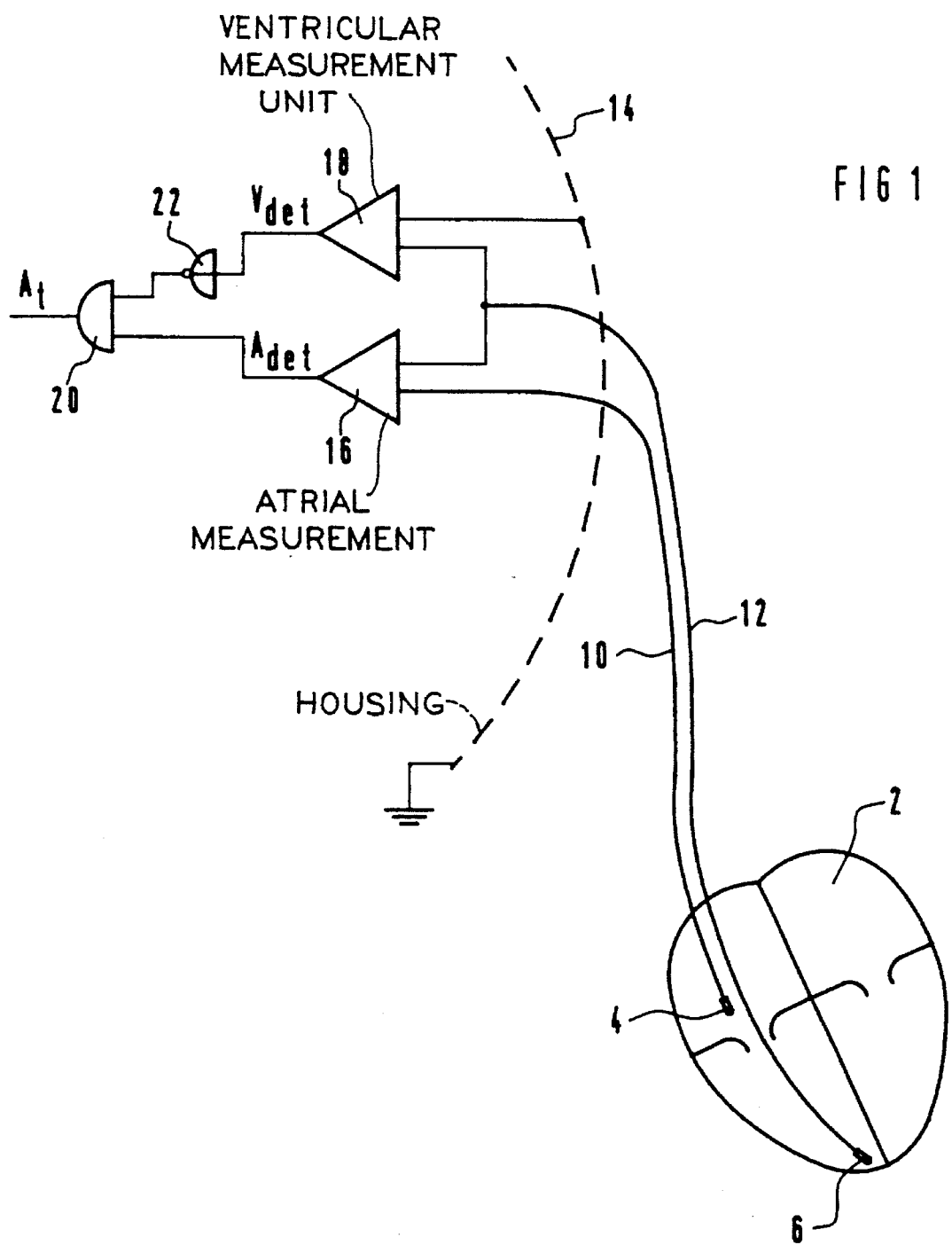
FIG. 1 is a schematic drawing of a heart stimulator constructed in accordance with the principles of the present invention with a bipolar electrode implanted in a heart.

FIG. 1 schematically shows an electrode system according to the invention implanted in a heart 2. The electrode system contains a bipolar electrode with one pole 4 arranged in the atrium and one pole 6 arranged in the ventricle. The electrode system has a single electrode cable containing respective leads 10 and 12 for the poles 4 and 6.

The stimulator housing is schematically indicated at 14.

The leads 10 and 12 are connected to input terminals of an atrial measurement unit 16. The lead 12 is connected in a like manner to one of the input terminals of a ventricular measurement unit 18. The other input terminal of the ventricular measurement unit 18 is connected to the stimulator housing 14.

The atrial measurement unit 16 thus measures the signal between the poles 4 and 6. The atrial measurement unit 16, however, detects both atrial and ventricular electrical events, because the lead 12 from the ventricular pole 6 is directly connected to the measurement unit 16. The output signal from the measurement unit 16 is therefore connected to one of two input terminals of an AND gate 20. The output signal from the ventricular measurement unit 18 is supplied, via a negating (inverting) element 22 to the other input to the AND gate 20. An output signal $A_t$ is thus obtained from the output of the AND gate 20 when an atrial event is detected without the substantially contemporaneous detection of any ventricular event, occurring at about the time of the atrial detection. Monitoring of the ventricular signal must therefore be conducted for a sufficiently long period of time around the time the atrial event is detected. The output signal $A_t$ constitutes the detection of a genuine atrial event.

The ventricular measurement unit 18 emits an output signal $V_{det}$, which directly designates ventricular events.

Figure 2:
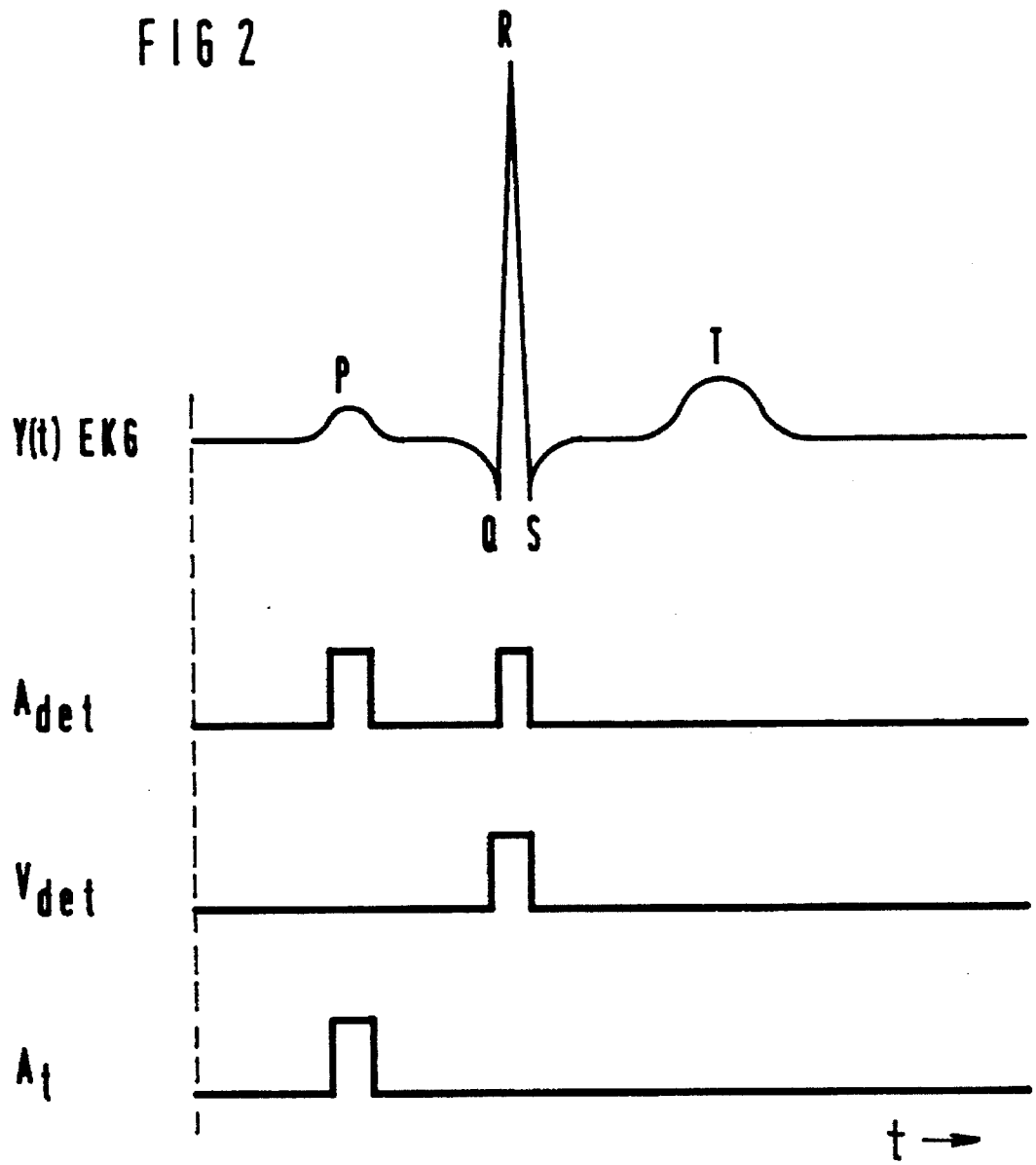
FIG. 2 shows signals obtained with the heart stimulator shown in FIG. 1.

FIG. 2 shows an extracorporeally-obtained electrocardiograph (EKG) signal Y(t) signals $A_{det}$ and $V_{det}$ in the form of output pulses appearing at the respective output terminals of the atrial and ventricular measurement units 16 and 18, and the output signal $A_t$ from the AND gate 20.

In the embodiment of FIG. 1, the atrial pole 4 is floating, i.e., it is not in direct contact with atrial tissue. The atrial pole 4 in the embodiment of FIG. 1, therefore, is not suitable for stimulation, and is used only for sensing atrial events.

Figure 3:
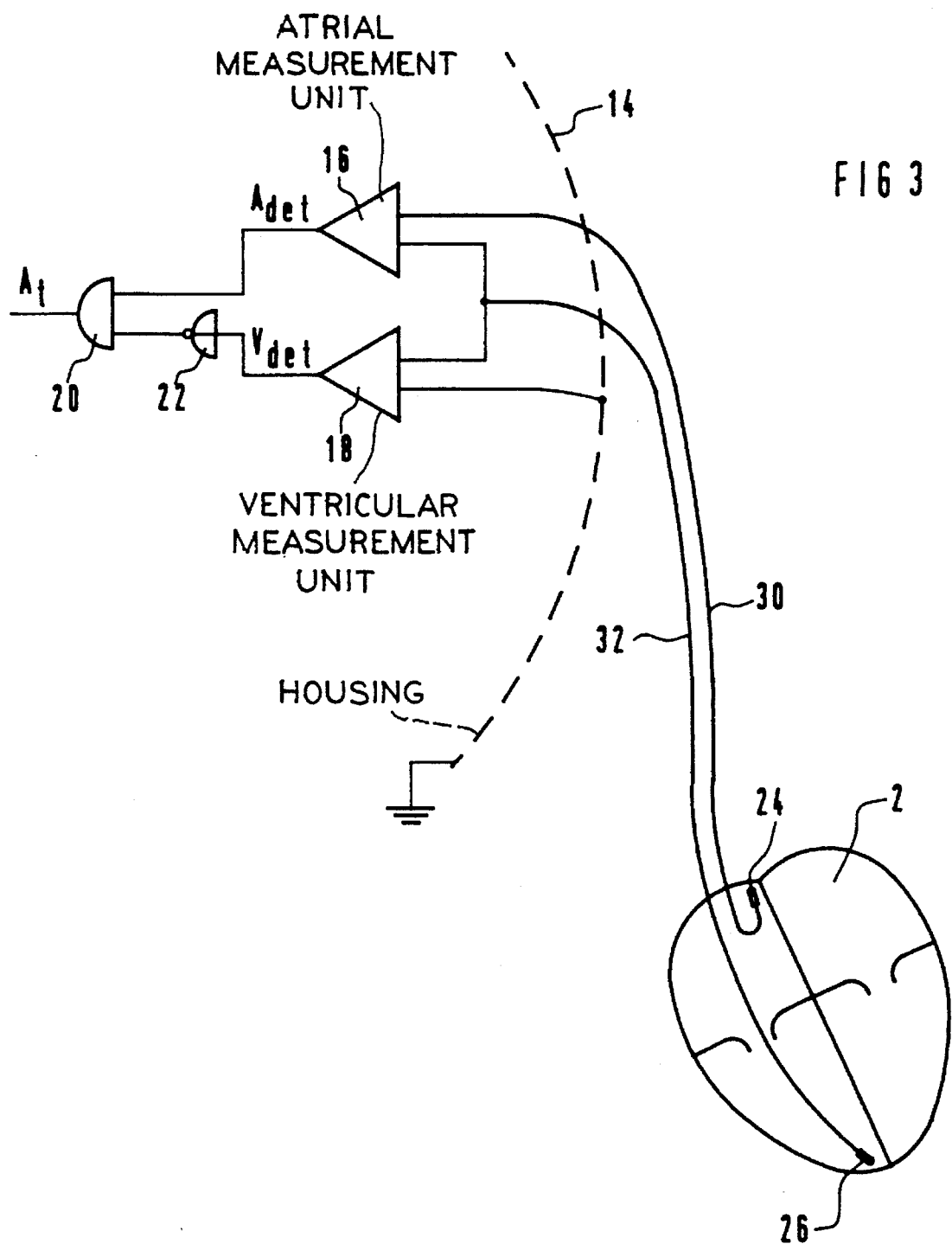
FIG. 3 schematically shows a heart stimulator constructed in accordance with the principles of the present invention having an implanted electrode system using two unipolar electrodes.

In the embodiment of FIG. 3, the electrode system contains unipolar electrodes 24 and 26 respectively disposed in the atrium and ventricle. In this embodiment, the atrial electrode 24 is arranged in direct contact with atrial heart tissue, making effective stimulation of the atrium also possible. FIG. 3 thus shows a DDD pacemaker having two leads 30 and 32 for the unipolar electrodes 24 and 26.

The sensing of atrial and ventricular events in the embodiment of FIG. 3 functions in the same manner as described in connection with the embodiment of FIG. 1.

Figure 4:
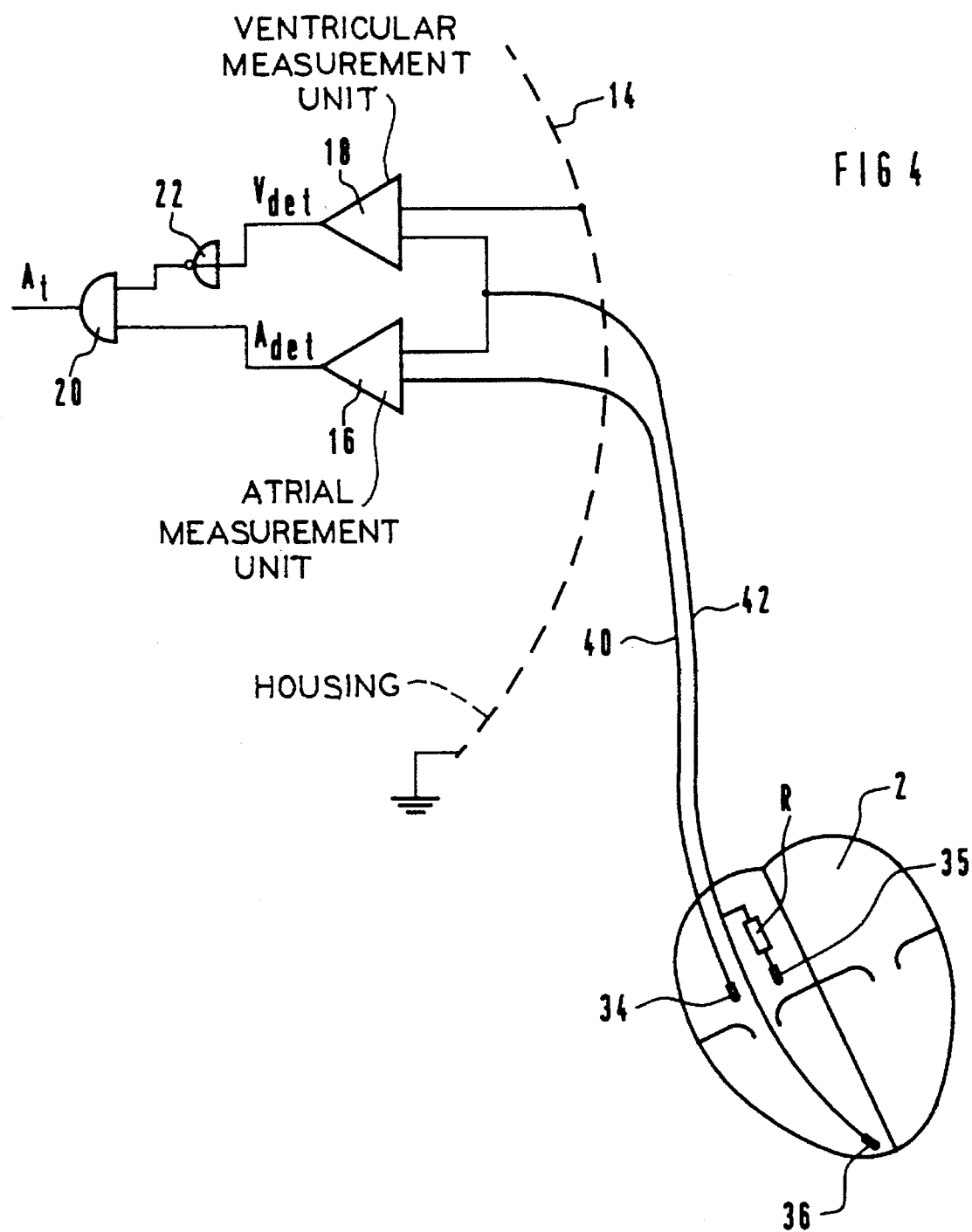
FIG. 4 schematically shows a further embodiment of the heart stimulator according to the invention with two poles in the atrium.

Another embodiment of a heart stimulator constructed in accordance with the principles of the present invention is shown in FIG. 4, similar to the embodiment of FIG. 1, but which includes an additional atrial pole 35. The atrial pole 35 is connected via a resistor R to a lead 42 running between the heart stimulator 14 and a ventricular sensing and stimulating pole 36. The value of the resistor is in the range of 1–20 kohms, and the resistor size is selected so that no stimulation occurs in the atrium through the lead 42, since the pole 36 in the ventricle has a lower resistance. The atrial pole 34 may also be connected to its lead 40 through a resistor, so that a balanced impedance is attained between the two atrial poles 34 and 35.

In this embodiment, detection of ventricular signals takes place in the same manner as described in the embodiments of FIGS. 1 and 3. The ventricular signal is normally much stronger than the atrial signal, and the sensitivity of the ventricular measurement unit 18 is therefore set so that only the relatively strong ventricular signals are detected, but not the weak atrial signals.

Detection of atrial events is made from the signal between the poles 34 and 35 in the atrium and between the pole 34 in the atrium and the pole 36 in the ventricle. When atrial cardiac activity is present, a differential signal is obtained between the pole 34 and the poles 35 and 36, the combination of the poles 35 and 36 serving as an signal is a measurement of atrial activity. The atrial measurement unit 16, however, also detects ventricular events, because the lead 42 sensing ventricular activity is connected to the atrial measurement unit 16. Ventricular activity is detected both by the unipolar ventricular detector 18 and by the differential atrial detector 16, whereas atrial events are detected only by the atrial detector 16. For this reason, logic gates 20 and 22 are used to define genuine atrial events as being atrial events which are detected without substantially contemporaneous ventricular detections, as described above.

The selection of atrial and ventricular events can be performed in some other manner than using the logic gates 20 and 22, as in the above-described embodiments.

Figure 5:
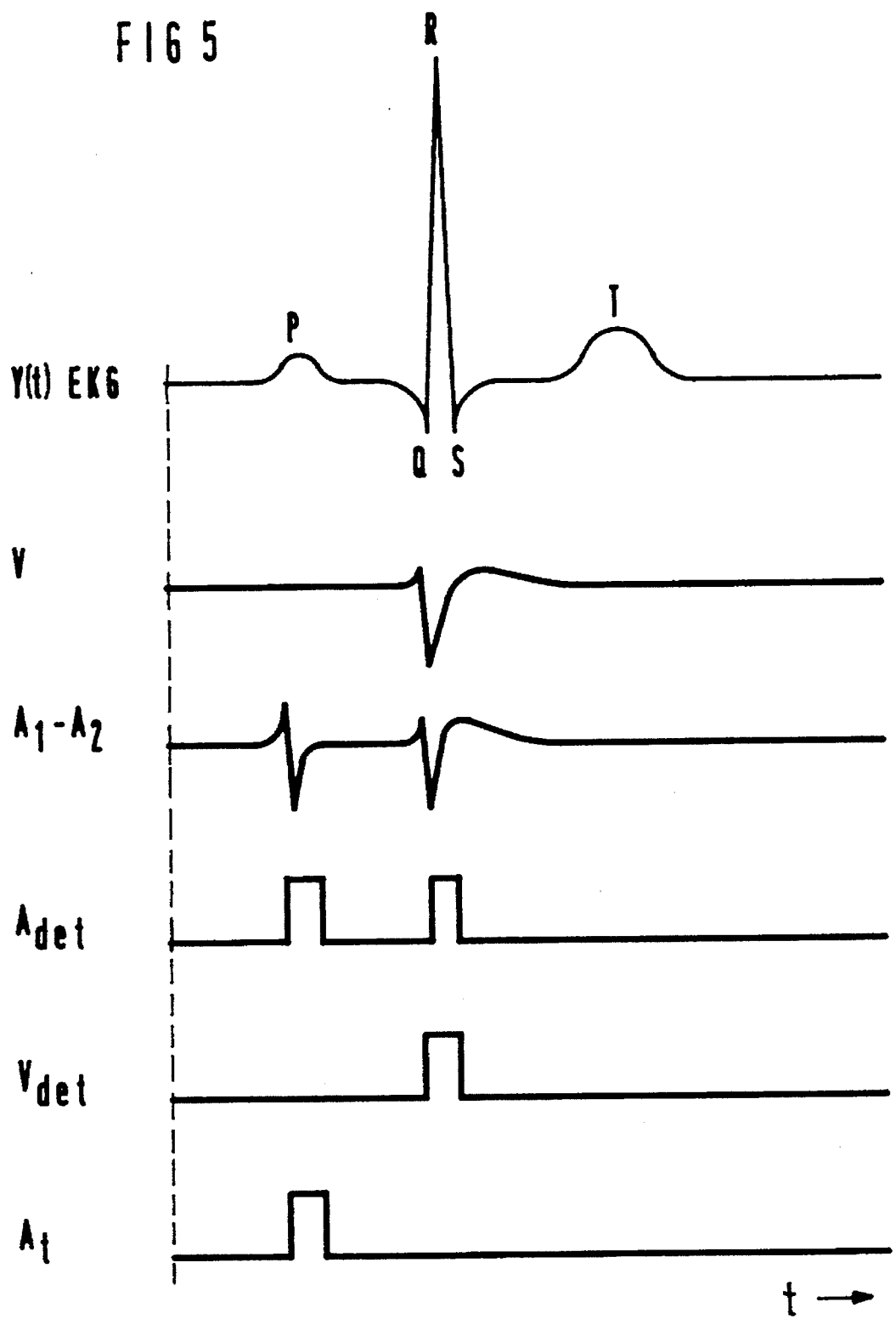
FIG. 5 shows signals obtained with the embodiment of the invention shown in FIG.4.

FIG. 5 shows the chronology of the different signals obtained in the embodiment of FIG. 4. A conventional surface electrocardiogram signal Y(t) is shown at the top of FIG. 5, followed by a signal V which is the signal picked-up by the ventricular pole 36. Below that is shown a differential signal $A_1 - A_2$, which is the differential signal between the two leads 40 and 42. The signal $A_{det}$ designates the output signal from the atrial measurement unit 16, and the signal $V_{det}$ designates the output signal from the ventricular measurement unit 18. The last signal $A_t$ designates the output signal from the AND gate 20. The signal $A_t$ thus designates genuine atrial events, i.e., the P-wave in the electrocardiogram, and $V_{det}$ designates genuine ventricular events, i.e., the QRS complex in the electrocardiogram.

Figure 6:
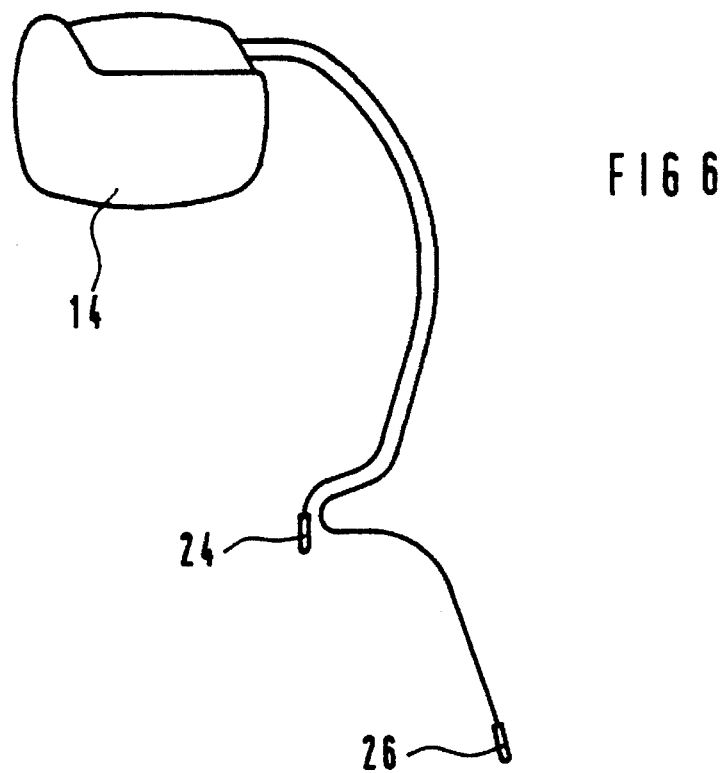
FIGS. 6 and 7 respectively schematically show practical implementations of the embodiments of FIGS. 3 and 4.

FIG. 6 schematically illustrates one implementation of the type of heart stimulator according to the invention, as shown in FIG. 3, wherein the electrode leads 30 and 32 are bent in the atrial area so that the electrode 24 comes into contact with atrial tissue after implantation.

Figure 7:
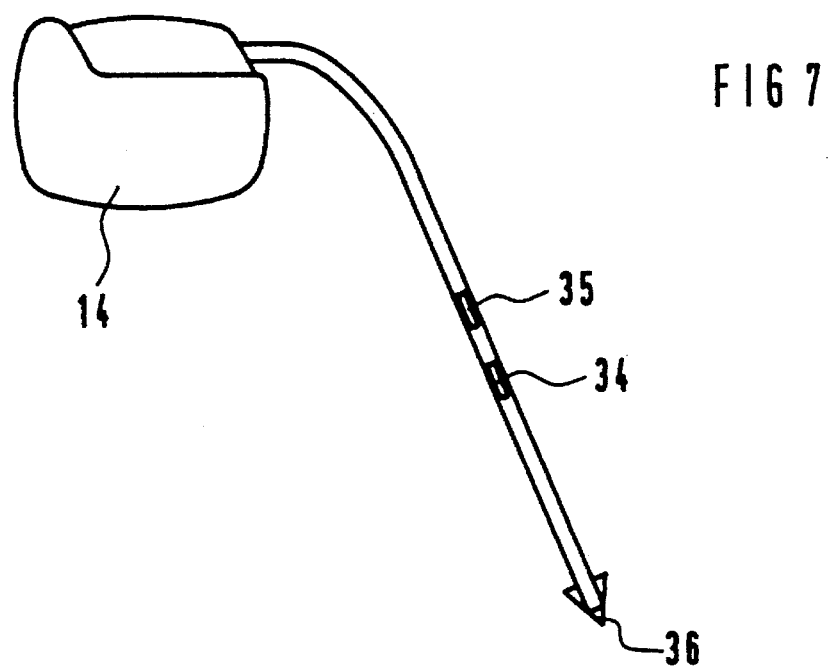

FIG. 7 schematically illustrates a practical implementation of the embodiment of FIG. 4.

FIG. 8 shows signals picked up by the heart stimulator constructed in accordance with the principles of the present invention in experiments conducted with a pig. The measurements were made using the embodiment shown in FIG. 3, with one well-positioned electrode in the atrium and another electrode in the ventricle. The upper signal channel CH1 shows the signal measured between the atrial and ventricular poles, i.e., the atrial signal, and the second signal channel CH2 shows the signal measured between the ventricular pole and the stimulator housing, i.e., the ventricular signal. In FIG. 8, atrial events are designated $A_e$ and ventricular events $V_e$. As can be seen in FIG. 8, the atrial signal CH1 includes both atrial and ventricular events, whereas the ventricular signal CH2 only shows ventricular events. "Genuine" atrial events can be extracted from the measured atrial signal CH1 using the above-described logic gates, applied to the atrial signal CH1.

The above-described embodiments of the invention have been set forth in the context of a heart stimulator in the form of pacemaker. The principles of the present invention, however, can also be used in heart stimulators such as defibrillators.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart stimulator comprising:

a housing;

a pulse generator contained in said housing;

electrode means for detecting atrial and ventricular activity including a pole adapted to be arranged in the atrium of a heart and a pole adapted to be arranged in the ventricle of said heart;

means for measuring atrial activity connected for measuring a signal between said pole adapted to be arranged in the atrium and at least said pole adapted to be arranged in the ventricle; and means for measuring ventricular activity connected for measuring a signal between said pole adapted to be arranged in the ventricle and said housing.

2. A heart stimulator as claimed in claim 1 wherein said electrode means comprises at least one bipolar electrode having one pole thereon comprising said pole adapted to be arranged in the atrium and another pole thereon comprising said pole adapted to be arranged in the ventricle.

3. A heart stimulator as claimed in claim 1 wherein said electrode means comprises two unipolar electrodes respectively adapted to be arranged in the atrium and ventricle and respectively carrying said pole adapted to be arranged in the atrium and said pole adapted to be arranged in the ventricle.

4. A heart stimulator as claimed in claim 1 further comprising logic means connected to said means for measuring atrial activity and said means for measuring ventricular activity for approving signals from said means for measuring atrial activity as genuine atrial events only if no signal is supplied from said means for measuring ventricular activity within a specified period of time around a time at which said means for measuring atrial activity generates an atrial signal.

5. A heart stimulator as claimed in claim 1 wherein said electrode means comprises a first lead running from said pulse generator into said atrium and carrying said pole arranged in the atrium and a second lead running from said pulse generator to the ventricle and carrying said pole arranged in the ventricle, said second lead having a further pole thereon arranged in the atrium and a resistor connected between said further pole and said second lead, said means for measuring atrial activity being connected between said first and second leads and wherein said means for measuring atrial activity comprises means connected for measuring a signal between said pole adapted to be arranged in the atrium and said pole adapted to be arranged in the ventricle and said further pole adapted to be arranged in the atrium carried on said second lead.

6. A heart stimulator as claimed in claim 1 wherein said pole adapted to be arranged in the atrium comprises a pole adapted to be arranged in the atrium as a floating pole.

7. A heart stimulator as claimed in claim 1 wherein said electrode means comprises means adapted for placing said pole adapted to be arranged in the atrium in contact with atrial tissue for electrically stimulating said atrial tissue.

* * * * *